United States Patent [19]

Radford

[11] 3,991,762
[45] Nov. 16, 1976

[54] ASPIRATING DEVICE FOR PATIENT VENTILATION APPARATUS

[76] Inventor: F. Richard Radford, 3722 S. 182nd, No. B209, Seattle, Wash. 98188

[22] Filed: Sept. 30, 1974

[21] Appl. No.: 510,504

[52] U.S. Cl. .............. 128/276; 128/2 M; 128/214.4; 128/351; 128/DIG. 9
[51] Int. Cl.² .................................. A61M 1/00
[58] Field of Search .................. 128/276–278, 128/349 R, 350 R, 351, 214.2, 214.4, DIG. 9, DIG. 16, 217

[56] References Cited
UNITED STATES PATENTS

| | | | |
|---|---|---|---|
| 2,584,450 | 2/1952 | Holt et al. | 128/351 |
| 2,893,395 | 7/1959 | Buck | 128/DIG. 9 |
| 2,937,643 | 5/1960 | Elliot | 128/214.4 |
| 3,017,880 | 1/1962 | Brook | 128/351 |
| 3,335,723 | 8/1967 | Waldman, Jr. | 128/214.4 |
| 3,757,771 | 9/1973 | Ruegg et al. | 128/214.4 |
| 3,774,604 | 11/1973 | Danielsson | 128/214.4 |
| 3,825,001 | 7/1974 | Bennet et al. | 128/DIG. 16 |
| 3,894,540 | 7/1975 | Bonner, Jr. | 128/214.4 |

Primary Examiner—Robert W. Michell
Assistant Examiner—Henry S. Layton
Attorney, Agent, or Firm—Christensen, O'Connor, Garrison & Havelka

[57] ABSTRACT

An aspirating device for a patient ventilation apparatus comprising a catheter cartridge, including an elongated catheter tube housed in an enclosing, protective housing, and a vacuum coupling mechanism is disclosed. A wheel, affixed to the proximal (vacuum) end of the catheter tube is housed in the vacuum coupling mechanism in a manner which allows access to the wheel. The protective housing includes a flexible envelope and sealing coupling elements. The flexible envelope allows the distal (patient) end of the catheter tube to be inserted into and withdrawn from the trachea of a patient. The wheel allows the catheter tube to be rotated during withdrawal. A port formed in the distal end element allows the outer surface of the catheter tube to be irrigated by a suitable cleansing solution during withdrawal of the catheter tube from the trachea. Further, a medication port, located in the vacuum coupling mechanism, in combination with a valve, allows medication to be inserted into the catheter tube. A suitable coupling element couples both the aspirating device and a suitable resuscitating apparatus to the trachea of a patient.

7 Claims, 4 Drawing Figures

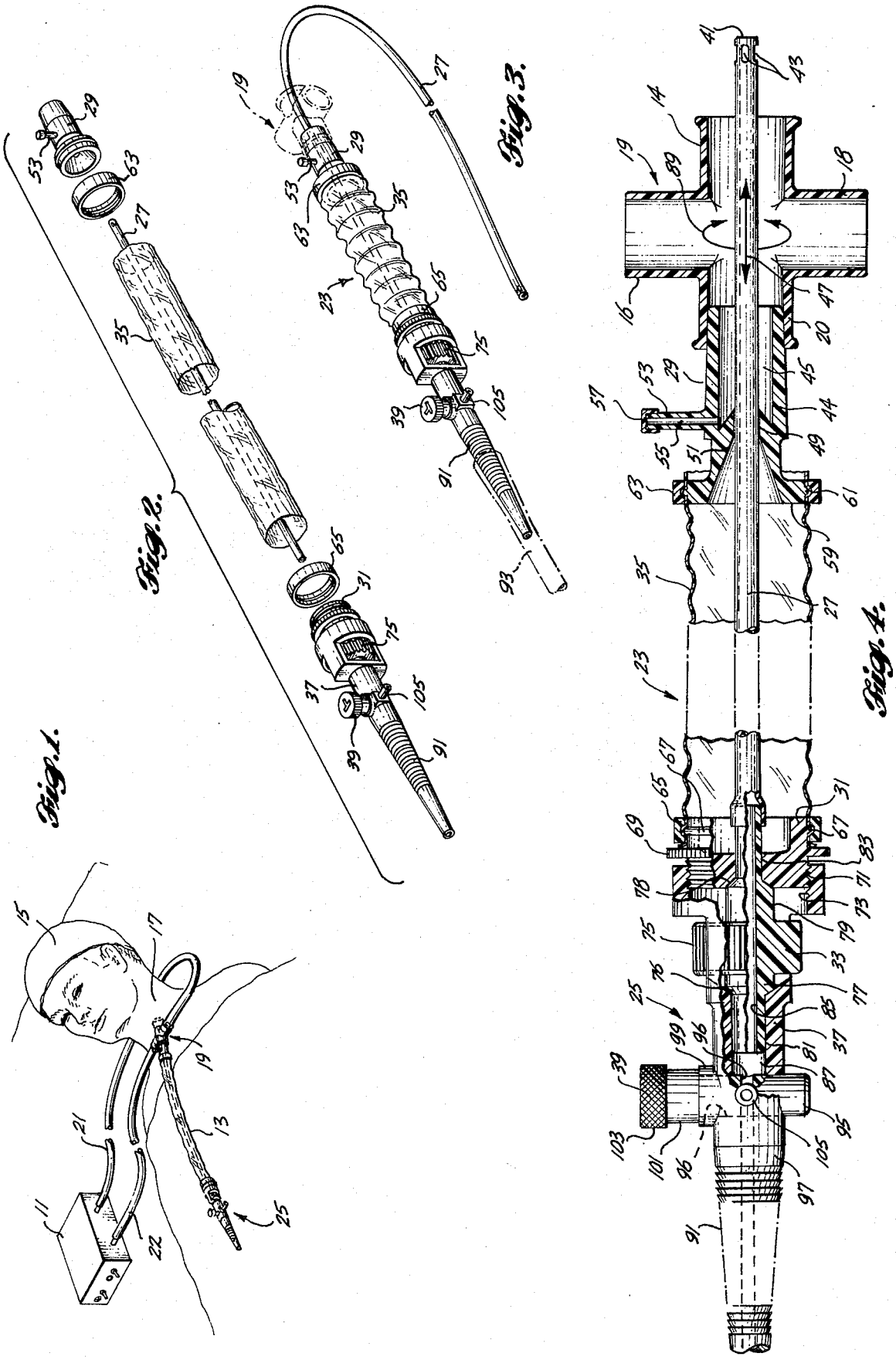

ASPIRATING DEVICE FOR PATIENT VENTILATION APPARATUS

BACKGROUND OF THE INVENTION

This invention is directed to patient ventilation apparatus and, more particularly, to an aspirating device suitable for use in a patient ventilation apparatus to remove fluid accumulations from the trachea and bronchi of a patient during resuscitation.

Various mechanical apparatus for ventilating a patient have been proposed and are in use. These apparatus range from simple endotracheal tubes adapted to prevent physical contact between a rescuer and a victim during mouth-to-mouth resuscitation to relatively complicated mechanical systems adapted to provide a flow of oxygenated air to a victim through a coupling mechanism. The coupling mechanism may include a nasal mask, an oral mask, a nasal and oral mask, or a tracheal connector fitted to the victim's trachea during a tracheostomy. While such apparatus have been proved to be satisfactory for ventilation purposes, the majority of such apparatus presently in use have a major disadvantage. Specifically, during patient ventilation, fluids frequently collect in the trachea and bronchi. These fluids can occlude the trachea and thus inhibit ventilation. In order to remove the occlusion, it is necessary for the fluids to be aspirated. In the past, aspiration has been performed by removing the ventilation apparatus and inserting into the trachea a suitable catheter tube connected to a vacuum source. The vacuum then sucks the fluid from the trachea and bronchi. Thereafter, the ventilation apparatus is reattached to the patient and ventilation is resumed.

The primary disadvantage of the foregoing procedure is the likelihood that the patient will enter one or another of several undesirable states when the respiratory support apparatus is removed. Among these states are hypoxia, hypoventilation, and hypercapnia. Moreover, the patient has a predisposition to cardiac arrhythmias, extreme discomfort and dyspnea.

Another disadvantage of the foregoing procedure relates to the aspirating device used. Many such devices are produced so as to be disposable and are provided sterile in a sealed container. Because of their nature and construction, they are only suitable for a single use. Thus, if several successive aspirating operations—spaced between ventilation—are necessary, several such devices must be used because each rapidly becomes unsterile after it is removed from the patient. Obviously, the necessity to use multiple devices is more expensive than desired.

Therefore, it is an object of this invention to provide a new and improved aspirating device suitable for use with ventilating apparatus.

It is also an object of this invention to provide an aspirating device that allows a catheter tube to be repeatedly inserted and removed from the trachea of a patient without it being contaminated by outside sources.

It is a still further object of this invention to provide an aspirating device which is readily, rapidly inserted into the trachea of a patient without requiring the removal of an associated ventilating apparatus.

It is yet another object of this invention to provide a disposable cartridge suitable for use in an aspirating device, said cartridge being suitable for repeated use by a single patient.

SUMMARY OF THE INVENTION

In accordance with principles of this invention, an aspirating device for ventilating apparatus is provided. The aspirating device comprises a catheter tube adapted to be inserted into and withdrawn from the trachea of a patient. The catheter tube has its proximal (vacuum) end affixed to a wheel adapted to rotate the tube during withdrawal. A protective housing surrounds the catheter tube in a manner such that moisture and other material on the external surface of the tube are removed when the tube is withdrawn.

In accordance with further principles of this invention, the protective housing comprises a flexible envelope, and end sealing elements. One end sealing element seals in the region where the wheel is coupled to the catheter tube. The other end sealing element seals the distal (patient) end of the catheter tube. The flexible envelope allows the end sealing elements to be moved toward and away from one another as the catheter tube is inserted into and withdrawn from the trachea of a patient.

In accordance with yet other principles of this invention, the catheter tube and protective housing form a disposable catheter cartridge.

In accordance with still further principles of this invention, a vacuum coupling mechanism surrounds the wheel and includes apertures which allow access to the wheel. The vacuum coupling mechanism includes channels adapted to allow a vacuum source to be applied to the catheter tube. The vacuum end sealing element is threaded into the vacuum coupling so as to apply pressure against various abutting surfaces adapted to form seals. The pressure also creates friction adapted to control the amount of torque necessary to create wheel rotation. In addition, the vacuum coupling mechanism includes a three-way valve which allows medication to be inserted via a medication port into the catheter tube.

In accordance with further principles of this invention, the patient end sealing element includes an irrigation port which allows the exterior of the catheter tube to be cleansed by a suitable solution as the catheter tube is withdrawn from the trachea.

In accordance with still further prnciples of this invention, the coupling element adapted to connect a patient to a ventilating apparatus, also couples the aspirating device of the invention to the patient.

It will be appreciated from the foregoing brief summary that the invention provides a relatively uncomplicated aspirating device suitable for use with a ventilating apparatus. Because the device is coupled to the patient via the same coupling element that connects the patient to the ventilating apparatus, the ventilating apparatus does not need to be removed from the patient during aspiration. Further, because the catheter tube, which provides a conduit for aspiration, is surrounded by a protective envelope in a sealed manner, extention and withdrawal of the catheter tube from the trachea of the patient is preformed without loss of relative sterility. In addition, because the catheter tube can be rotated during withdrawal, it is easily manipulated within the patient's airway. Not only does the invention provide an improved aspirating device, it also provides mechanisms for cleansing the exterior surface of the catheter tube as it is removed and for inserting medicants either through the catheter tube or, if desired, in the region surrounding the catheter tube, via the irrigation port. Hence, the invention not only overcomes the disadvantages of prior art devices briefly discussed above, but also provides additional features not provided by such devices.

BRIEF DESCRIPTION OF THE DRAWINGS

The foregoing objects of many of the attendant advantages of this invention will become more readily appreciated as the same becomes better understood by reference to the following detailed description when taken in conjunction with the accompanying drawings wherein:

FIG. 1 is a pictorial view illustrating a ventilating apparatus, and an aspirating device formed in accordance with the invention, connected to a patient;

FIG. 2 is an exploded perspective view of a preferred embodiment of the invention;

FIG. 3 is an assembled perspective view of a preferred embodiment of the invention with the catheter tube extended; and, FIG. 4 is a cross-sectional view of a preferred embodiment of the invention.

DESCRIPTION OF THE PREFERRED EMBODIMENT

FIG. 1 is a perspective view of a ventilating apparatus 11 and an aspirating device 13 connected to a patient 15. While the inventive aspirating device is illustrated and described herein as connected to the patient 15 via a tracheostomy connector, it will be appreciated that, with suitable modifications, the invention can also be utilized with oral and/or nasal coupling elements, if desired.

In any event, FIG. 1 illustrates the ventilating apparatus 11 connected to the throat 17 of the patient 15 via a tracheostomy connector 19. Rather than a conventional T-shaped connector adapted only for connection to a ventilating apparatus, the illustrated tracheostomy connector 19 is X-shaped i.e., it has four branch legs 14, 16, 18 and 20 (FIG. 4). One of the legs 14 of the tracheostomy connector 19 is connected to a tracheostomy tube located within an aperture formed in the throat 17 of the patient 15 as a result of a tracheostomy operation. Two of the other legs 16 and 18 are connected to the ventilating apparatus 11 via an input tube 21 and a return tube 22. The fourth leg 20 of the tracheostomy connector 19 is connected to the aspirating device 13 forming the present invention. The leg 20 connected to the aspirating device 13 is aligned with the leg 14 mounted in the tracheostomy aperture, as illustrated in FIG. 4.

In general, the aspirating device of the invention comprises an elongated, replaceable cartridge 23 and a vacuum coupling mechanism 25. For purposes of discussion, the proximal ends of various elements are defined as the ends nearest the vacuum source (not illustrated) coupled to the vacuum coupling mechanism 25 and the distal ends are defined as the ends nearest the patient 15.

The catheter cartridge 23 generally comprises: a catheter tube 27; a patient coupling element 29; a vacuum coupling element 31; a wheel 33; and, a protective envelope 35. The vacuum coupling mechanism 25 generally comprises a vacuum coupling housing 37; and, a three-way vavle element 39. If desired, the wheel may form a part of the vacuum coupling mechanism rather than the catheter cartridge, provided suitable changes are made in the manner of attachment described herein.

The catheter tube 27 is a soft, flexible tube adapted to be inserted into the trachea/bronchial tree of a patient for the purpose of removing fluid secretions using suction. Preferably, the catheter tube is formed of a suitable plastic. While flexible, the catheter tube must have structural strength adequate to prevent undesired twisting distortion when normal torque is applied to it by the wheel 33 in the manner hereinafter described. Moreover, its structural strength must be adequate to resist compression distortion (bending) when a normal compressive force adapted to move it through a seal formed in the patient coupling element 29 is applied. The distal end 41 of the catheter tube 27 includes a plurality of peripheral apertures 43 through which secretions can enter its interior. In addition, secretions can also enter the catheter tube through its distal tip which is open. It should be noted here that catheter distal ends, other than the one specifically illustrated and described, can also be utilized by the invention.

The patient coupling element 29 includes a generally tubular body 44 surrounding a cylindrical longitudinal aperture 45 along which the catheter tube 27 moves back and forth as illustrated by the arrow 47. A conical projection 51 pointing toward the distal end of the catheter tube 27 and projecting into the longitudinal aperature 45 forms a seal 49 about the catheter tube 27. The seal 49, as will be better understood from the following description of the operation of the invention, is adapted to prohibit accumulated fluid secretions from adhering to the outer surface of the catheter tube from being withdrawn into the protective envelope. Further, the seal 49 prohibits air from passing into the interior of the protective envelope. In this regard, it should be noted that the seal 49 may define either a fixed radii aperture or an adjustable radii aperture, if flexible materials are utilized. The outer surface of the distal end of the patient coupling element 27 surrounding the longitudinal aperture 45 is slightly tapered in a manner which allows it to be tightly inserted into the "aspiration" leg 20 of the tracheostomy connector 19.

The patient coupling element 29 also includes an irrigation port 55 formed in a radial projection 53. The irrigation port 55 lies between the tip of the tapered end of the patient coupling element 29 and the seal 49 and provides a passageway adapted to allow an irrigating fluid to flow about the exterior surface of the catheter tube 27 as it is being withdrawn from the trachea of a patient. Preferably the irrigating fluid is a suitable sterile fluid. The irrigating fluid is withdrawn either via the return tube 22 running to the resuscitating unit or via the catheter tube 27 as a result of a suitable suction force being applied. A cap 57 is provided to cap the outer end of the irrigation port 55 when it is not connected to a suitable irrigation fluid source.

The non-tapered end of the patient coupling element 29 includes an enlarged cylindrical shoulder 5 from which an encompassing peripheral projection 61 extends. One end of the protective envelope 35 (which is preferably a flexible cylinder, as hereinafter described) surrounds the projection 61 and is affixed to the non-tapered end by a retaining ring 63. The retaining ring 63 includes an inner indentation into which the projection 61 presses the related portion fo the protective envelope.

The protective envelope 35 is, as indicated above, generally cylindrical in shape. Preferably it is formed of a flexible, lightweight, translucent plastic material. The protective envelope is adapted to protect the outer surface of the catheter tube 27 yet allow a user of the invention to manipulate the catheter along its longitudinal axis through the seal 49.

A second retaining ring 65 retains the other end of the protective envelope 35 in a sealed manner about the vacuum coupling element 31. More specifically, the vacuum coupling element 31 is also generally cylindrical in shape and includes a peripheral projection 67 near its distal end. The second retaining ring 65 includes an inner indentation in which the peripheral projection lies. The end of the protective envelope 35 is clamped between the second retaining ring and the peripheral projection. In this manner, a flexible protective housing is provided.

Located on the remote side of the second retaining ring 65 and formed as a unitary portion of the vacuum coupling element 31 is an enlarged cylindrical projection 69. The outer surface of the enlarged cylindrical projection includes indentations which allow it to be readily gripped. Located on the other side of the enlarged cylindrical projection region 69 is a threaded region 71. The threaded region 71 extends to the proximal end of the vacuum couplng element and is adapted to fit into a theaded aperture 73 formed in the vacuum coupling housing 37.

The wheel 33 has a main cylindrical body 74 having an indented periphery which allows it to be readily gripped. Axially aligned with, and extending outwardly from either side of the main cylindrical body 74 are cylindrical hubs 77 and 79. The diameters of the hubs are less than the diameter of the main cylindrical body. The hubs terminate at conical shoulders 76 and 78 that diverge inwardly. The conical shoulders terminate where they join axially aligned outwardly extending cylindrical shafts 81 and 83. The shafts 81 and 83, the shoulders 76 and 78, the hubs 77 and 79 and the main body 75 are, preferably, all formed in a unitary manner of a suitable hard plastic. As noted above, the wheel may form a part of the vacuum coupling element 31 rather than a part of the replaceable catheter cartridge 23.

The vacuum coupling element 31 includes an aperture lying along the longitudinal axis defined by its cylindrical configuration. Starting from the threaded end of the vacuum coupling element, the aperture is first defined by an inwardly diverging cone having a size similar to the size of the distal conical shoulder 78 of the wheel 33. The cone region is followed by a cylindrical region having a diameter equal to the diameter of the distal shaft 83 of the wheel. Beyond the cylindrical region is an enlarged undercut region that extends to the distal end of the vacuum coupling element. The distal conical shoulder 78 and shaft 83 of the wheel lie in their associated sized regions of the aperture in the vacuum coupling element in a manner such that the shaft 83 extends into the enlarged undercut region.

The proximal end of the catheter tube 27 is stretch fitted about the shaft 83 lying in the enlarged undercut region of the vacuum coupling element. The wheel 33 includes an axial aperture 85 which provides a passageway through the wheel into the interior of the catheter tube 27. At this point it should be noted that the length of the protective envelope is such that the distal end of the catheter tube 27 extends slightly beyond the seal 29 in the patient coupling element 29 when the protective envelope is fully extended.

The vacuum coupling housing 37 is an elongated coupling element having a central cylindrical aperture 87 that is adapted to provide a passageway between the aperture 85 in the wheel and a tube 93 adapted to be connected to a suitable vacuum source (not shown). As indicated above, one end of the vacuum coupling housing includes a threaded aperture 73 within which the threaded end of the vacuum coupling element 31 lies. The other end 91 of the vacuum coupling housing tapers inwardly and includes peripheral coupling barbs. Immediately inwardly from the threaded aperture 73 lies the main body 75 of the wheel 33. A portion of the vacuum coupling housing 37 surrounding the main body is removed to allow access thereto. Continuing inwardly from the main body 75, beyond the proximal hub 77 of the wheel is a conical aperture followed by a cylindrical aperture. These apertures are positioned and sized so as to receive the proximal conical shoulder 76 and the proximal shaft 81 of the wheel 33.

Sealing between the wheel and its surrounding element is provided in the conical shoulder regions. More specifically, the distal conical shoulder 78 abuts the vacuum coupling element 31 and the proximal conical shoulder abuts the vacuum coupling housing 37. The pressure in these abutment regions is controlled by the extent to which the vacuum coupling element 31 is threaded into the threaded aperture 73 in the vacuum coupling housing 37. In addition, the amount of the compressive force created by the extent of inward threading also controls the amount of rotational force necessary to be applied to the wheel 75 in order for the catheter tube 27 to be rotated in either direction as illustrated by the arrow 89. In other words, the friction between these abutting elements controls the amount of torque necessary to rotate the catheter.

Located between the conical end 91 of the vacuum coupling housing 37 and the termination of the proximal shaft 81 of the wheel 33 is the three-way valve element 39. Three-way valve element 39 includes a tubular cylindrical section 95 having the T-shaped aperture 95 96 lying in a plane located at right angles to its longitudinal axis. The tubular cylindrical section 95 is mounted in a cylindrical aperture 96 formed in the vacuum coupling housing 37 and located at right angles to an elongated aperture 97 extending longitudinally through the conical end 91.

A shoulder 99 lying outside the cylindrical aperture 96 locates the tubular cylindrical section 95 such that the T-shaped aperture is aligned with the elongated aperture 97. The elongated aperture is also aligned with the aperture 85 in the wheel 33. Thus, the position of the T-shaped aperture controls whether or not a passageway exists between the elongated aperture 97 and the aperture 85 in the wheel. Located beyond the shoulder 99 is a cylindrical outward projection 101 that includes a knurled peripheral region 103 adapted to allow the three-way valve element to be readily, manually positioned.

A medication port projection 105 located at right angles to the elongated aperture 97 is aligned with the T-shaped aperture 96. Thus, the T-shaped aperture in the valve element 39 is also aperture to allow the medication port 105 to communicate via the wheel 33 with the catheter tube 27. In this manner medications can be given to the patient via the catheter tube 27. In addition, the T-shaped aperture is adapted to allow the elongated aperture 97 to communicate with the medication port if desired. Obviously which communication path exists depends upon the rotational position of the valve element 39.

It will be appreciated at this point that the invention comprises an aspirating device suitable for use with a ventilating apparatus. The aspirating device includes a catheter tube and a mechanism for readily and rapidly inserting it into the trachea of a patient. The tube can be moved in its longitudinal direction and rotated as it is longitudinally moved. Not only does the invention provide for a readily insertable catheter tube, the catheter tube can be withdrawn in a relatively sterile manner when its use is no longer required. Thus, it remains ready for reuse, as needed. Not only does the apparatus of the invention provide a mechanism for cleaning the outer surface of the tube during withdrawal but also provides a protective envelope around the withdrawn tube to prevent contamination from the operating personnel and other contamination sources in the patient's environment. The apparatus also provides a mechanism for allowing medication to be given to a patient via the catheter tube.

Because the catheter tube can be readily inserted and withdrawn, without being exposed to an unsterile environment, it can be used and reused on a particular patient. In this regard, it should be noted that the cartridge 23, which includes the catheter tube, the protective envelope, and the patient and vacuum coupling elements, can be made disposable, if desired. In this regard also, it should be noted that all of these elements are, preferably formed of suitable rigid or flexible plastic materials, as necessary. Alternatively, the entire unit—both the cartridge and the vacuum connecting mechanism 25—can be formed as a disposable unit, if desired.

While a preferred embodiment of the invention has been illustrated and described, it will be appreciated that various changes can be made therein without departing from the spirit and scope of the invention. For example, patient connectors other than a tracheostomy connector can be utilized with the invention, if desired. In addition, valve structures other than the specific valve structure illustrated and described can be utilized. Moreover, other means for attaching the protective envelope to the coupling elements can be utilized. Hence, the invention can be practiced otherwise than as specifically described herein.

The embodiments of the invention in which an exclusive property or privilege is claimed are defined as follows:

What is claimed is:

1. An aspirating device suitable for use in removing undesirable secretions from the trachea of a patient during ventilation, said aspirating device comprising:
    A. a catheter cartridge including:
        1. a catheter tube suitable for insertion into the trachea of a patient; and,
        2. a protective housing surrounding at least the majority of the length of said catheter tube when said catheter tube is withdrawn, said protective housing adapted to allow one end of said catheter tube to be extended from said housing into the trachea of a patient and withdrawn therefrom;
    B. a rotational mechanism including a wheel, said wheel including shafts extending axially outwardly from either side thereof, one of said shafts being affixed to the other end of said catheter tube, said wheel further including a longitudinal aperture extending axially through said shafts such that said longitudinal aperture in said one of said shafts is in communication with said other end of said catheter tube; and,
    C. a vacuum coupling mechanism including a vacuum coupling housing, said wheel mounted inside of said vacuum coupling housing, said vacuum coupling housing including at least one aperture which allows access to said wheel such that said wheel can be manually rotated, the manual rotation of said wheel causes said catheter tube to be rotated, said vacuum coupling housing including an aperture having one end in communication with the other end of the longitudinal aperture formed in said wheel, the other end of said aperture in said vacuum coupling housing adapted for connection to a vacuum source.

2. An aspirating device as claimed in claim 1 wherein said protective housing comprises:
    a patient coupling element adapted to surround said catheter tube nearest the end thereof adapted to be inserted into the trachea of a patient, said patient coupling element including a seal which surrounds the outer periphery of said catheter tube;
    a vacuum coupling element including an aperture through which a shaft forming a portion of said rotational mechanism extends, said shaft being affixed to said other end of said catheter tube; and,
    a protective envelope surrounding said catheter tube and affixed to said patient coupling element and said vacuum coupling element, said protective envelope formed of a flexible material adapted to compress when said vacuum coupling element and said patient coupling element are moved relatively toward one another, said movement causing said catheter tube to extend through said seal in said patient coupling element.

3. An aspirating device as claimed in claim 2 wherein said patient coupling element includes an irrigation port adapted to provide a communication path between a suitable irrigation fluid source and the outer periphery of said catheter tube on the side of said patient coupling element seal remote from said protective envelope.

4. An aspirating device as claimed in claim 3 including a connector suitable for connecting said aspirating device to a patient and also suitable for connecting said patient to a suitable ventilation source.

5. An aspirating device as claimed in claim 2 wherein said vacuum coupling housing includes a medication port and a valve, said valve adapted to connect said catheter tube either to said vacuum source or to said medication port.

6. In an aspirating device adapted to remove undesirable secretions from the trachea of a patient during ventilation wherein a catheter tube is inserted into the trachea of a patient by longitudinal and rotational movement of the catheter, the improvement comprising a disposable catheter cartridge, said disposable cartridge comprising:
    A. a catheter tube suitable for longitudinal insertion of one end into the trachea of a patient and withdrawl therefrom; and,
    B. a protective housing, said protective housing including;
        1. a patient coupling element mounted so as to surround said catheter tube nearest the end thereof suitable for insertion into the trachea of a patient, said patient coupling element including a seal surrounding said catheter tube and adapted to prevent fluid secretions located on the external suruface of said catheter from being withdrawn into said protective housing when said catheter tube is withdrawn into said protective housing and an irrigation port suitable for connection to a suitable irrigation source and in communication with the external surface of said catheter tube;

2. a vacuum coupling element located adjacent to the end of said catheter tube remote from the end thereof adapted to be inserted into the trachea of a patient; and, 3. a protective envelope extending between said patient coupling element and said vacuum coupling element and formed of a flexible plastic material that distorts and compresses when said vacuum coupling element and said patient coupling element are moved relatively toward one another, said movement causing said one end of said catheter tube to extend outwardly from said patient coupling element.

7. The improvement claimed in claim 6 including a wheel connected to said catheter tube in a manner such that rotation of said wheel causes said catheter tube to rotate.

* * * * *